(12) United States Patent
Kiilerich

(10) Patent No.: US 10,441,722 B2
(45) Date of Patent: Oct. 15, 2019

(54) DRUG DELIVERY DEVICE WITH SPRING MECHANISM

(71) Applicant: Novo Nordisk A/S, Bagsvaerd (DK)

(72) Inventor: Ebbe Kiilerich, Copenhagen NV (DK)

(73) Assignee: Novo Nordisk A/S, Bagsvaerd (DK)

(*) Notice: Subject to any disclaimer, the term of this patent is extended or adjusted under 35 U.S.C. 154(b) by 171 days.

(21) Appl. No.: 15/568,574

(22) PCT Filed: Apr. 29, 2016

(86) PCT No.: PCT/EP2016/059627
§ 371 (c)(1),
(2) Date: Oct. 23, 2017

(87) PCT Pub. No.: WO2016/174213
PCT Pub. Date: Nov. 3, 2016

(65) Prior Publication Data
US 2018/0154087 A1    Jun. 7, 2018

(30) Foreign Application Priority Data

Apr. 29, 2016 (EP) .................................... 15165735

(51) Int. Cl.
*A61M 5/315* (2006.01)
*A61M 5/20* (2006.01)

(52) U.S. Cl.
CPC .......... *A61M 5/31553* (2013.01); *A61M 5/20* (2013.01); *A61M 5/2033* (2013.01);
(Continued)

(58) Field of Classification Search
CPC .......... A61M 5/31528; A61M 5/31548; A61M 5/3155; A61M 5/31551; A61M 5/31553;
(Continued)

(56) References Cited

U.S. PATENT DOCUMENTS

| 5,104,380 A | 4/1992 | Holman et al. |
| 2011/0106008 A1 | 5/2011 | Kronestedt |

(Continued)

FOREIGN PATENT DOCUMENTS

| WO | 2006/003130 A1 | 1/2006 |
| WO | 2006045526 A1 | 5/2006 |

(Continued)

*Primary Examiner* — Andrew M Gilbert
(74) *Attorney, Agent, or Firm* — Wesley Nicolas

(57) ABSTRACT

A drug delivery device comprises an housing, an axially displaceable piston rod, a rotatable drive member, a spring housing, a torsion drive spring coupled to the spring housing respectively the drive member, dose setting means allowing a user to simultaneously set a dose amount to be expelled and strain the torsion drive spring correspondingly by rotation of the drive member, and a release member being axially moveable relative to the housing between a proximal initial position and an actuated distal release position. The spring housing is helically coupled to the housing such that the spring exerts a tangential force on the spring housing to thereby bias the spring housing in the proximal direction, whereby the spring housing thereby exerts a proximally directed biasing force on the release member. The spring housing can be moved helically in the distal direction when a distally directed force is exerted on the release member.

10 Claims, 7 Drawing Sheets

(52) U.S. Cl.
CPC ........ *A61M 5/3155* (2013.01); *A61M 5/3158* (2013.01); *A61M 5/31535* (2013.01); *A61M 5/31536* (2013.01); *A61M 5/31558* (2013.01); *A61M 5/31575* (2013.01); *A61M 5/31583* (2013.01); *A61M 5/31593* (2013.01)

(58) Field of Classification Search
CPC ............ A61M 5/31576; A61M 5/3158; A61M 5/31583
See application file for complete search history.

(56) References Cited

U.S. PATENT DOCUMENTS

| | | | | |
|---|---|---|---|---|
| 2011/0257604 | A1* | 10/2011 | Banik | A61M 5/484 604/209 |
| 2012/0165752 | A1* | 6/2012 | Holmqvist | A61M 5/31553 604/211 |
| 2012/0172811 | A1* | 7/2012 | Enggaard | A61M 5/20 604/193 |
| 2013/0204193 | A1* | 8/2013 | Holmqvist | A61M 5/20 604/189 |
| 2014/0114247 | A1 | 4/2014 | Karlsson et al. | |
| 2014/0350484 | A1* | 11/2014 | Kohlbrenner | A61M 5/20 604/222 |

FOREIGN PATENT DOCUMENTS

| | | |
|---|---|---|
| WO | 2006130100 A1 | 12/2006 |
| WO | 2008031235 A1 | 3/2008 |
| WO | 2010089418 A2 | 8/2010 |
| WO | 2011025448 A1 | 3/2011 |
| WO | 2012128699 A1 | 9/2012 |
| WO | 2014161952 A1 | 10/2014 |

* cited by examiner

DRUG DELIVERY DEVICE WITH SPRING MECHANISM

CROSS-REFERENCE TO RELATED APPLICATIONS

This application is a 35 U.S.C. § 371 National Stage application of International Application PCT/EP2016/059627 (published as WO 2016/174213), filed Apr. 29, 2016, which claims priority to European Patent Application 15165735.0, filed Apr. 29, 2015; the contents of which are incorporated herein by reference.

The present invention generally relates to drug delivery devices adapted to expel a user settable dose of drug from a cartridge. In a specific aspect the invention relates to a spring-driven device.

BACKGROUND OF THE INVENTION

In the disclosure of the present invention reference is mostly made to the treatment of diabetes, however, this is only an exemplary use of the present invention.

A general type of drug delivery devices suitable for delivery of a user set amount of drug comprises a spring which is strained during dose setting, the stored energy subsequently being used to expel the set dose of drug from a cartridge arranged in the device. The user usually strains a spring by rotating a rotatable dose setting member, the force thereby applied by the user being stored in the spring for later release. This type of drug delivery device may be provided either in the form of a pre-filled disposable device or in the form of a durable device adapted to be loaded with a drug cartridge by the user.

An example of a known "wind-up" drug delivery device having a pen-formed configuration and applying a torsion spring is disclosed in U.S. Pat. No. 5,104,380. In this wind-up device, or "auto-pen", the dose setting member is located at the proximal end and works such that when the user rotates the dose setting member the spring is strained and maintained in this strained position until the user releases the set dose by activating the latch provided on the side of the housing. WO 2012/128699 discloses a "wind-up" drug delivery device having means for setting a desired limit for the size of dose which can be set. The wind-up pens disclosed in U.S. Pat. No. 5,104,380 and WO 2012/128699 have the disadvantage that if a user sets a dose too large it is not possible to decrease the set dose. The user then has to release the latch mechanism thereby expelling the entire set dose before a new correct dose can be set and delivered.

Addressing this problem, wind-up pens in which the user can actually decrease the set dose prior to dosing has been proposed, see e.g. WO 2006/045526 and WO 2010/089418.

These "automatic" delivery devices are based on a spring which is tightened during dose setting and thereafter released to inject the set dose. If a user erroneously sets a dose higher than needed these injection devices has the possibility of lowering the set dose by rotating the dose setting member in an opposite rotational direction. Such dial-down mechanisms can therefore save the user from expelling expensive drug due to an erroneous dose setting.

In WO 2006/045526, the dial-up/dial-down mechanism is based on a flexible ratchet arm which is locked in a one-way engagement with a toothed ring. When the user sets a dose the dose setting button provided at the proximal end of the delivery device is rotated. This dose setting button is connected to the ratchet element via a longitudinal stretching tubular sleeve. The ratchet element is provided with a ratchet arm in a toothed engagement with the toothed ring such that the ratchet arm when the dose setting button is rotated locks against the force of the torsion spring in the subsequent teeth of the toothed ring thereby straining the torsion spring in incremental steps. In order to reduce the set size, the ratchet arm is actively pulled out of engagement with the toothed ring whereby the force accumulated in the torsion spring rotates the ratchet element rapidly backwards such that the ratchet arm engages the previous tooth in the toothed ring thereby lowering the set dose with one increment. In this way a releasable one-way ratchet mechanism is provided allowing a set dose to be diminished. The FlexTouch® and FlexPro® drug delivery devices provided by Novo Nordisk, Bagsværd, Denmark comprise a ratchet mechanism of the type disclosed in WO 2006/045526. WO 2011/025448 discloses a further drug delivery device comprising a ratchet mechanism of this type.

The dial-down arrangement known from WO 2006/045526 could be referred to as being an "active" dial-down arrangement as the ratchet arm needs to be radially and actively moved free of its toothed engagement in order to dial down the set dose size. An example of a "passive" dial-down arrangement is known from e.g. WO 2008/031235 disclosing a dose setting mechanism with a two-way ratchet.

As an alternative to the wind-up type of automatic drug delivery devices, devices have been proposed which are provided with a pre-strained spring in which sufficient energy is stored for expelling the entire dispensable amount of drug contained in a cartridge, e.g. 3 ml. The dose setting means will typically be similar to the above-described dial-up/dial-down arrangements allowing a user to set and adjust a dose to be expelled.

Having regard to the above, it is an object of the present invention to provide a drug delivery device of the automatic type which is simple and reliable and allows for cost-effective manufacturing. The device may comprise a reset-table dose setting mechanism, e.g. of the above-described "active" type.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a general aspect of the invention a drug delivery device is provided comprising or adapted to receive a drug-filled cartridge, the drug delivery device comprising a housing and an expelling assembly. The expelling assembly comprises a piston rod adapted to engage and axially displace a piston in a received cartridge in a distal direction to thereby expel a dose of drug from the cartridge, a drive member defining an axis, a spring housing, a torsion drive spring coupled to the spring housing respectively the drive member, dose setting means allowing a user to set a dose amount to be expelled, and a release member being axially moveable relative to the housing between a proximal initial position and an actuated distal release position. The spring housing is helically coupled to the housing, such that the spring exerts a tangential force on the spring housing to thereby bias the spring housing in the proximal direction. The spring housing is arranged to exert a proximally directed biasing force on the release member, and to be moved helically in the distal direction when a distally directed force is exerted on the release member.

In a more specific aspect of the invention a drug delivery device is provided comprising or adapted to receive a drug-filled cartridge, the drug delivery device comprising a housing and an expelling assembly. The expelling assembly comprises a piston rod adapted to engage and axially displace a piston in a received cartridge in a distal direction to thereby expel a dose of drug from the cartridge, a drive member defining an axis, a spring housing, a torsion drive spring coupled to the spring housing respectively the drive member, and dose setting means allowing a user to simultaneously set a dose amount to be expelled and strain the drive spring correspondingly by rotation of the drive member. The dose setting means comprises a dose setting member which during dose setting is rotationally coupled to the drive member and adapted to rotate in a first direction to set a dose, and a ratchet mechanism allowing the drive member to be held in a set rotational position against the bias of the strained drive spring. The expelling assembly further comprises release means adapted to release the strained drive spring to rotate the drive member to expel the set dose amount, the release means comprising a release member being axially moveable relative to the housing between a proximal initial position and an actuated distal release position. The spring housing is helically coupled to the housing, the spring exerting a tangential force on the spring housing to thereby bias the spring housing in the proximal direction, the spring housing exerts a proximally directed biasing force on the release member when actuated, and the spring housing can be moved helically in the distal direction when a distally directed force is exerted on the release member.

By the helical coupling between the spring housing and the housing the torsion drive spring provides a proximally directed bias force which when acting on the release member serves to return the latter after actuation. By this arrangement a given spring previously used to return the release member can be dispensed with or a further spring can be optimized for its primary function, e.g. when used in a ratchet mechanism.

In exemplary embodiments the release member is axially fixed relative to the drive member such that also the drive member is moved proximally by the proximally directed biasing force from the spring housing.

The dose setting member may be adapted to rotate in an opposed second direction to reduce a set dose. To achieve this, the ratchet mechanism may be designed to allow adjustment in both the first and the second direction.

In exemplary embodiments the ratchet mechanism is in the form of a releasable one-way ratchet mechanism allowing a set dose to be diminished. Alternatively, the ratchet mechanism may be in the form of a two-way ratchet mechanism allowing a set dose to be diminished.

The dose setting member may be a combined dose setting and release member being moveable from a proximal dose setting position to a distal spring release position.

In an exemplary embodiment the spring housing is helically coupled to the housing by means of protrusions received in corresponding inclined slots. The slots may be formed in the housing, the spring housing or in both.

In an alternative exemplary embodiment the spring housing is helically coupled to the housing by means of proximally open inclined slots extending from the housing, and distally extending inclined fingers extending from the spring housing and adapted to slidingly engage the inclined slots. Indeed, the housing portions provided between the slots could be considered fingers just as the gaps provided between the fingers could be considered slots.

The spring may be pre-strained allowing a well-defined biasing force to be provided for even small set doses. Alternatively the spring may be pre-strained with an amount of energy stored allowing the dispensable amount of drug in a cartridge to be expelled. Such an arrangement would typically be relevant for a pre-filled disposable device.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin.

BRIEF DESCRIPTION OF THE DRAWINGS

In the following exemplary embodiments of the invention will be further described with reference to the drawings, wherein.

In the figures like structures are mainly identified by like reference numerals.

DESCRIPTION OF EXEMPLARY EMBODIMENTS

Figure 1A:
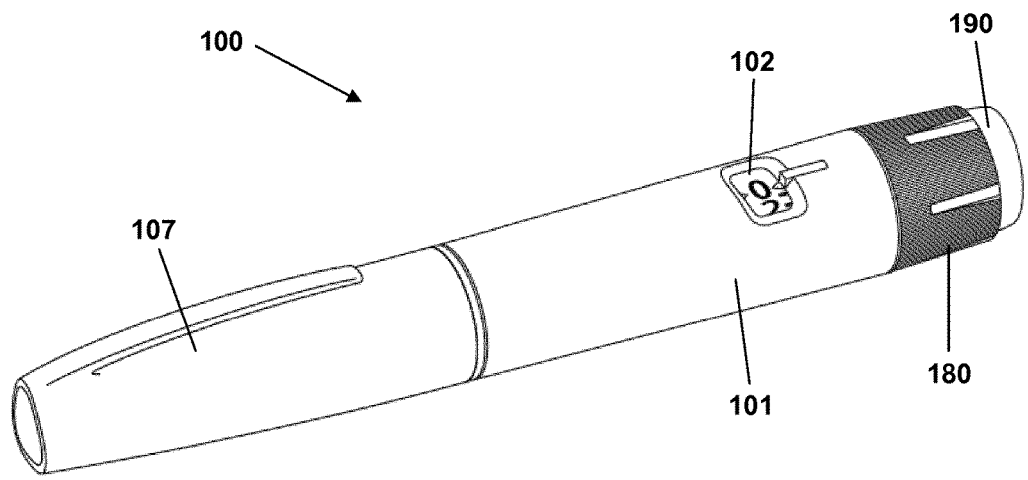
FIGS. 1A and 1B show an embodiment of a drug delivery device.

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Before turning to embodiments of the present invention per se, an example of a "generic" resettable dial-up/dial down automatic drug delivery device will be described, such a device providing the basis for the exemplary embodiment of the present invention.

The pen device 100 comprises a cap part 107 and a main part having a proximal body or drive assembly portion with a housing 101 in which a drug expelling mechanism is arranged or integrated, and a distal cartridge holder portion in which a drug-filled transparent cartridge 113 with a distal needle-penetrable septum is arranged and retained in place by a cartridge holder attached to the proximal portion, the cartridge holder having openings allowing a portion of the cartridge to be inspected. Distal coupling means 115 allows a needle assembly to be releasably mounted in fluid communication with the cartridge interior. The cartridge is provided with a piston driven by a piston rod forming part of the expelling mechanism and may for example contain an insulin, GLP-1 or growth hormone formulation. A proximal-most rotatable dose setting member 180 serves to manually set a desired dose of drug shown in display window 102 and which can then be expelled when the button 190 is actuated. Depending on the type of expelling mechanism embodied in the drug delivery device, the expelling mechanism may comprise a torsion spring as in the shown embodiment which is strained during dose setting and then released to drive the piston rod when the release button is actuated. More specifically, during dose setting a drive member to which the spring is connected is rotated to a rotational position corresponding to the set dose, the drive member thereby being in an energized state. A scale drum with dose size numerals is coupled to the drive member such that the size of the currently set dose is shown in the display window, e.g. by means of a threaded connection with the housing. To prevent the drive member from rotating the dose setting mechanism is provided with a holding mechanism, which in the shown embodiment is in the form of a ratchet mechanism. When the user desires to expel the set dose the button is actuated whereby the drive member is brought into engagement with the piston rod drive mechanism and the holding mechanism subsequently released.

Figure 1B:
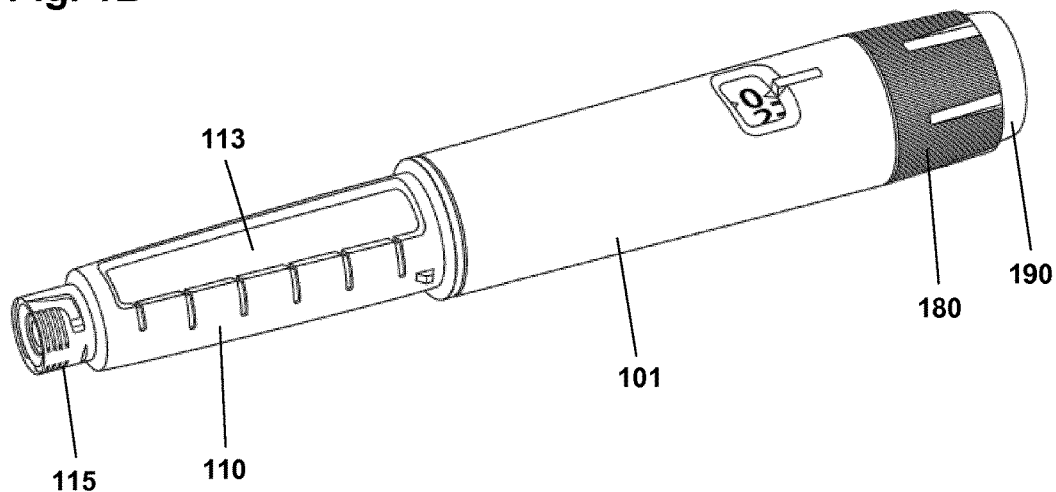

Although FIGS. 1A and 1B show a drug delivery device of the pre-filled type, i.e. it is supplied with a pre-mounted cartridge and is to be discarded when the cartridge has been emptied, in alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

With reference to FIGS. 2-6 a first exemplary embodiment of the present invention per se, a resettable dose setting mechanism for a drug delivery device, will be described. The mechanism basically comprises a housing portion 201, a drive tube 260, a torsion drive spring 255 arranged between the housing and the drive tube, a transmission member 240, a dose setting member 280, a release button 290 and a return spring 295.

A detailed description of the working principle of the mechanism will be given below, however, first some of the central components of the dose setting mechanism will be described in detail.

Figure 2:
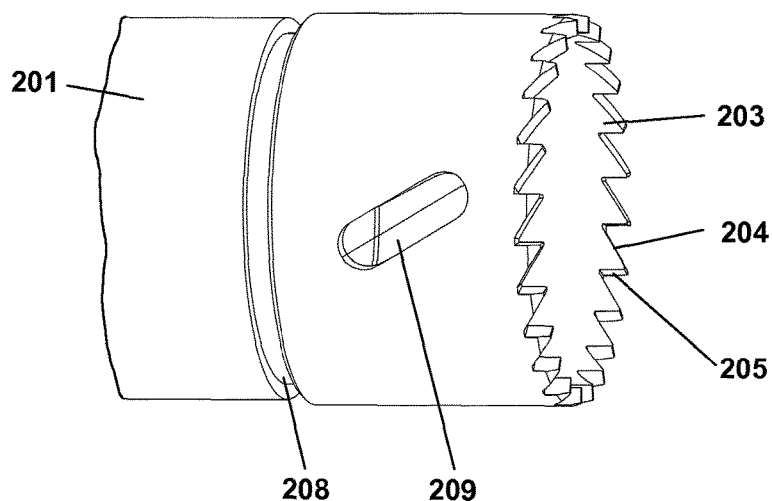
FIG. 2 shows a ratchet part of an exemplary embodiment of a drug delivery device.

Turning to FIG. 2 a proximal portion of a tubular housing member 201 defining a longitudinal axis is shown. The housing member comprises a circumferential proximal edge with a plurality of ratchet teeth structures 203 (here: 24), each tooth having a triangular configuration with an inclined ratchet surface 204 and a stop surface 205 oriented perpendicularly to the housing member cross-sectional plane. The housing further comprises a circumferential groove 208 adapted to engage the dose setting member and arranged between the groove and the proximal end a number of inclined slots 209 (here: three) adapted to engage a spring housing (see below). In this way a first ratchet part coupled non-rotationally to the housing and comprising a plurality of ratchet teeth is formed. As appears, in this embodiment the first ratchet part is formed integrally with the tubular housing member.

Figure 3:
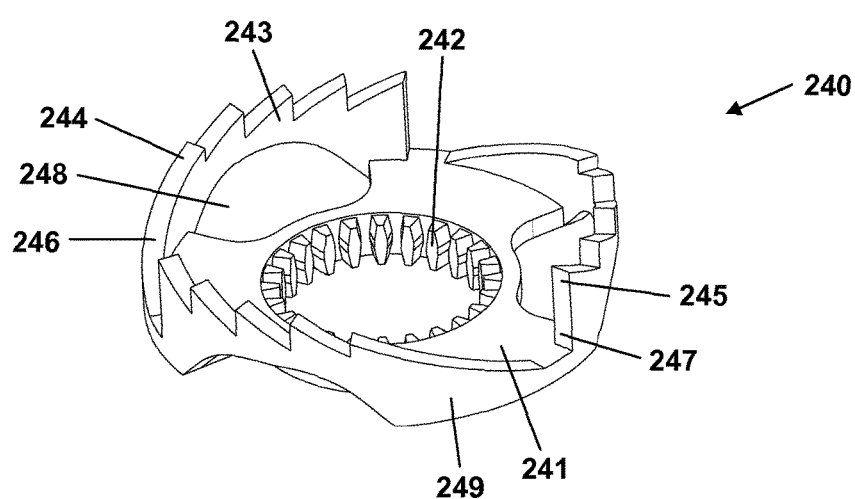
FIG. 3 shows a further ratchet part of the exemplary embodiment.

FIG. 3 shows the dose setting member 280 having a generally tubular configuration with an outer cylindrical surface with a plurality of longitudinally arranged ridges 281 providing a gripping surface, and an inner cylindrical surface comprising a at the distal end a number of circumferential flange portions 288 adapted to be rotationally arranged in the housing member circumferential groove. The inner surface further comprises a number of triangular "drive-release" og "drive-lift" control ratchet structures 283 (here: three) adapted to engage the transmission member as will be described below, each drive-lift control structure comprising a longitudinally oriented drive surface 287 and an inclined lift surface 286. In the following description the term "drive-lift" will be used.

Figure 4:
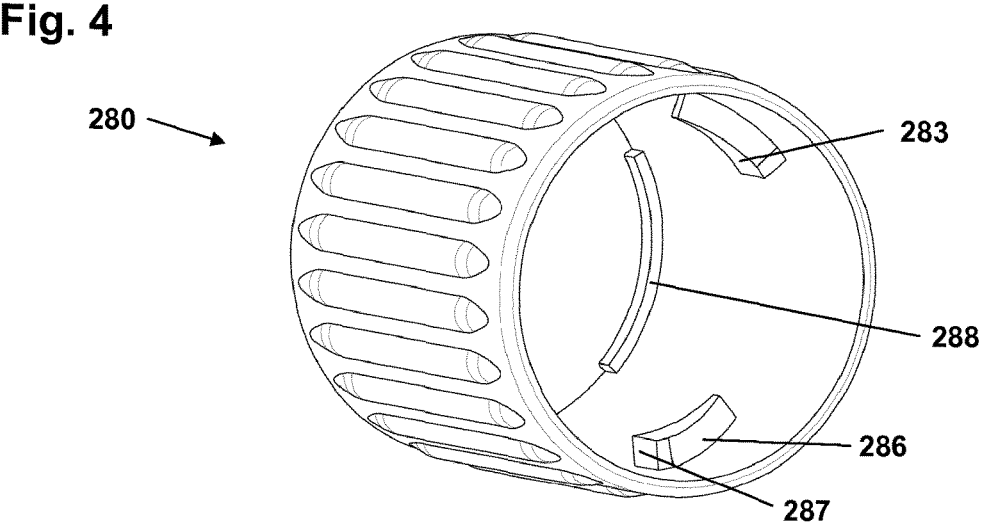
FIG. 4 shows a dose setting member of the exemplary embodiment.

FIG. 4 shows the transmission member 240 having a ring-shaped body portion 241 with a central opening provided with a plurality of longitudinally arranged splines 242 adapted to slidingly engage corresponding spline grooves on the drive tube. The transmission member further comprises a number of ratchet sections 249 (here: three) between which are formed three drive sections. Each ratchet section comprises a number of ratchet teeth 243 adapted to engage the housing member ratchet teeth 203 to provide a one-way ratchet. In this way a second ratchet part is formed. For a given ratchet section the leading inclined ratchet surface 244 is extended to form a lift surface 246, just as the trailing stop surface 245 is also extended longitudinally to form a drive surface 247. In this way each drive section is defined between an extended ratchet surface and an extended stop surface. Corresponding to each ratchet section an opening 248 is formed in the body portion to allow passage of a release button leg portion (see below).

Figure 5:
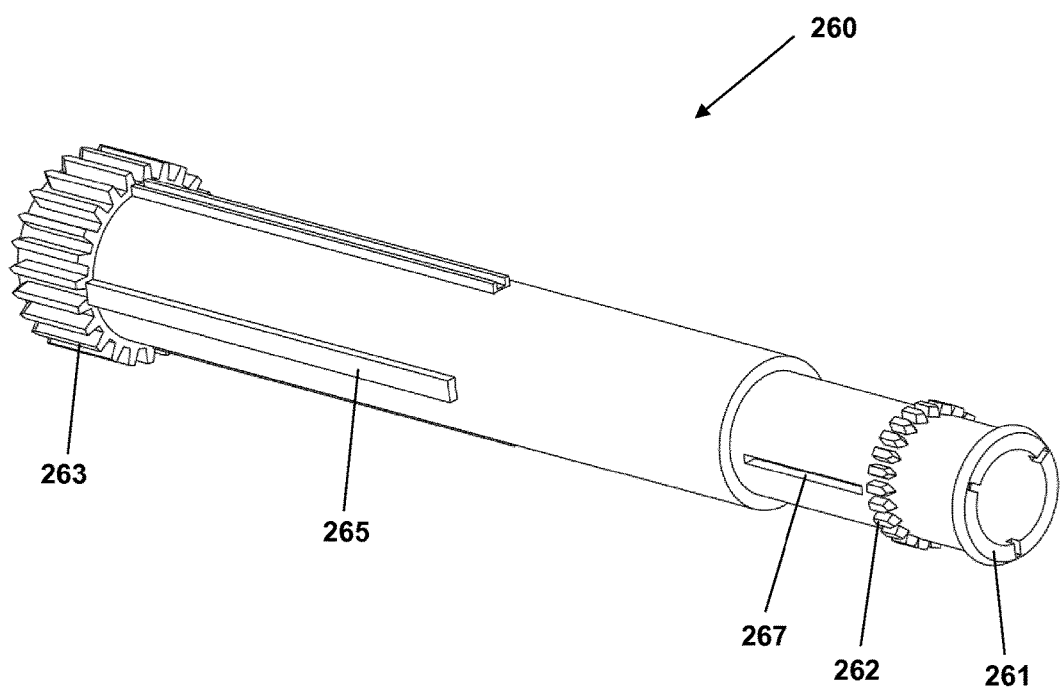
FIG. 5 shows a drive member of the exemplary embodiment.

FIG. 5 shows the drive tube 260 having a proximal-most circumferential flange 261, a proximal array of circumferential splines 262 and a distal array of circumferential splines 263. The flange is adapted to engage release button snap members 291, the proximal splines are adapted to engage the transmission member splines 242, and the distal splines are coupling splines adapted to axially engage the piston driver 230 during actuation. The drive tube further comprises an axial slot 267 for attaching the inner end of the drive spring as well as a number of splines 265 adapted to interface with a scale drum. As appears, one of the splines is different allowing it to rotationally mate with a corresponding scale drum spline.

Figure 6:
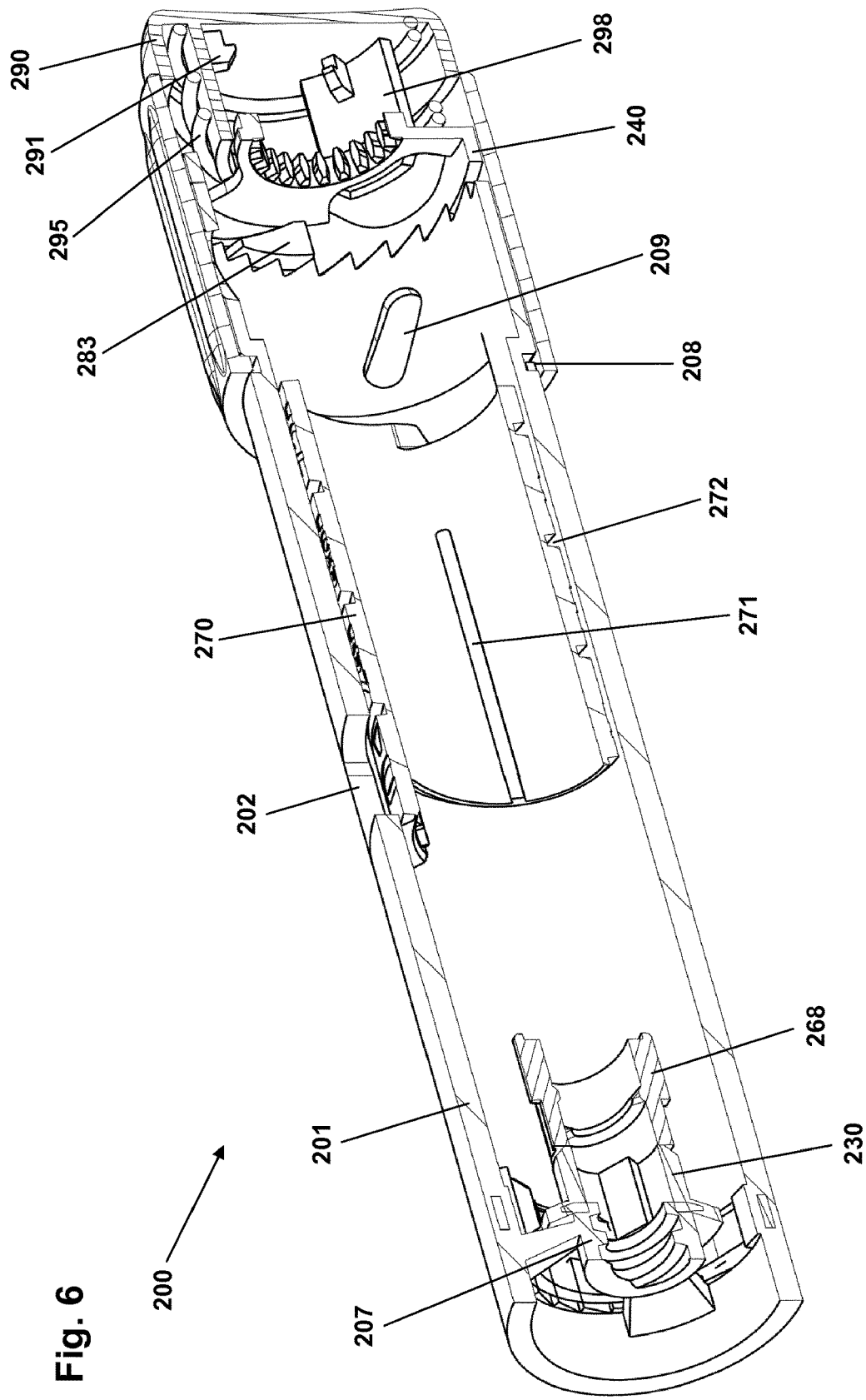
FIG. 6 shows in cross-section the exemplary embodiment in a partly assembled state.

Turning to FIG. 6 the housing member proximal portion, the dose setting member, the transmission member and the release button are shown in an assembled state. The figure further shows the proximal portion of a scale 270 drum provided with an inner longitudinal spline 271 for engagement with the drive tube and an outer helical groove 272 for threaded connection with the housing inner surface. To allow the ratchet interface to be visible, the drive tube and the torsion spring have been omitted in FIG. 6.

More specifically, the dose setting member 280 is mounted rotationally free but axially locked on the housing member by means of the flanges arranged in the circumferential housing groove 208. The transmission member 240 is mounted non-rotationally on the drive tube (see FIG. 7) by means of a splined connection allowing the transmission member to move axially relative to both the drive tube and the dose setting member. Further, the release button 280 is mounted rotationally free but axially locked to the proximal end of the drive tube by means of a number of snap members 291 engaging the proximal flange 261. The release button further comprises a number of leg portions 298 adapted to be moved through the transmission member openings 248. A bias means in form of a return spring 295 is arranged between the transmission member and the release button, the return spring urging the transmission member ratchet teeth 243 into engagement with the housing member ratchet teeth 203 as shown. As can also be seen in FIG. 6 one of the drive-lift ratchet control structures 283 is arranged corresponding to a transmission member drive section, the two drive surfaces and the two lift surfaces engaging each other. As appears, in the engaged position the ratchet prevents the transmission member, and thus the drive tube, from being turned counter-clockwise.

When setting a dose the dose setting member is rotated clockwise. As the drive surfaces 287 of the drive-lift ratchet control structures 283 are in engagement with the corresponding drive surfaces 247 on the transmission member the latter is forced to rotate together with the dose setting member to the desired rotational position, this resulting in the transmission member ratchet teeth passing over the housing ratchet teeth during which the transmission member is moved back and forth due to the inclined ratchet teeth, the return spring and the splined connection with the drive tube. The dose can be set in increments corresponding to one ratchet tooth which e.g. for a given insulin delivery device typically will correspond to one unit (IU) of insulin formulation. During dose setting the drive spring is strained correspondingly. To ensure a proper drive torque also for smaller doses the drive spring is pre-strained in the initial state.

When decreasing a set dose the dose setting member is rotated counter-clockwise whereby a gap is created between the drive surfaces on the drive-lift ratchet control structure 283 respectively the transmission member. However, as the inclined lift surfaces 286 of the drive-lift control structures are in engagement with the corresponding lift surfaces 246 on the transmission member the latter is moved proximally against the return spring until the transmission member ratchet teeth just disengages the housing ratchet teeth, at which point the force from the strained spring will rotate the drive tube counter-clockwise and thereby also the transmission member, this resulting in the inclined lift surfaces disengaging each other. As a consequence the transmission member can be moved distally by the return spring whereby the ratchet teeth will re-engage, this corresponding to the previously set dose having been decreased by one increment. If the user continuous to rotate the dose setting member counter-clockwise the set dose will continue to be reduced by one increment for each back and forth movement of the transmission member. At the same time the scale drum is also rotated counter-clockwise and the dose size shown in the display window 202 is reduced correspondingly.

Figure 7:
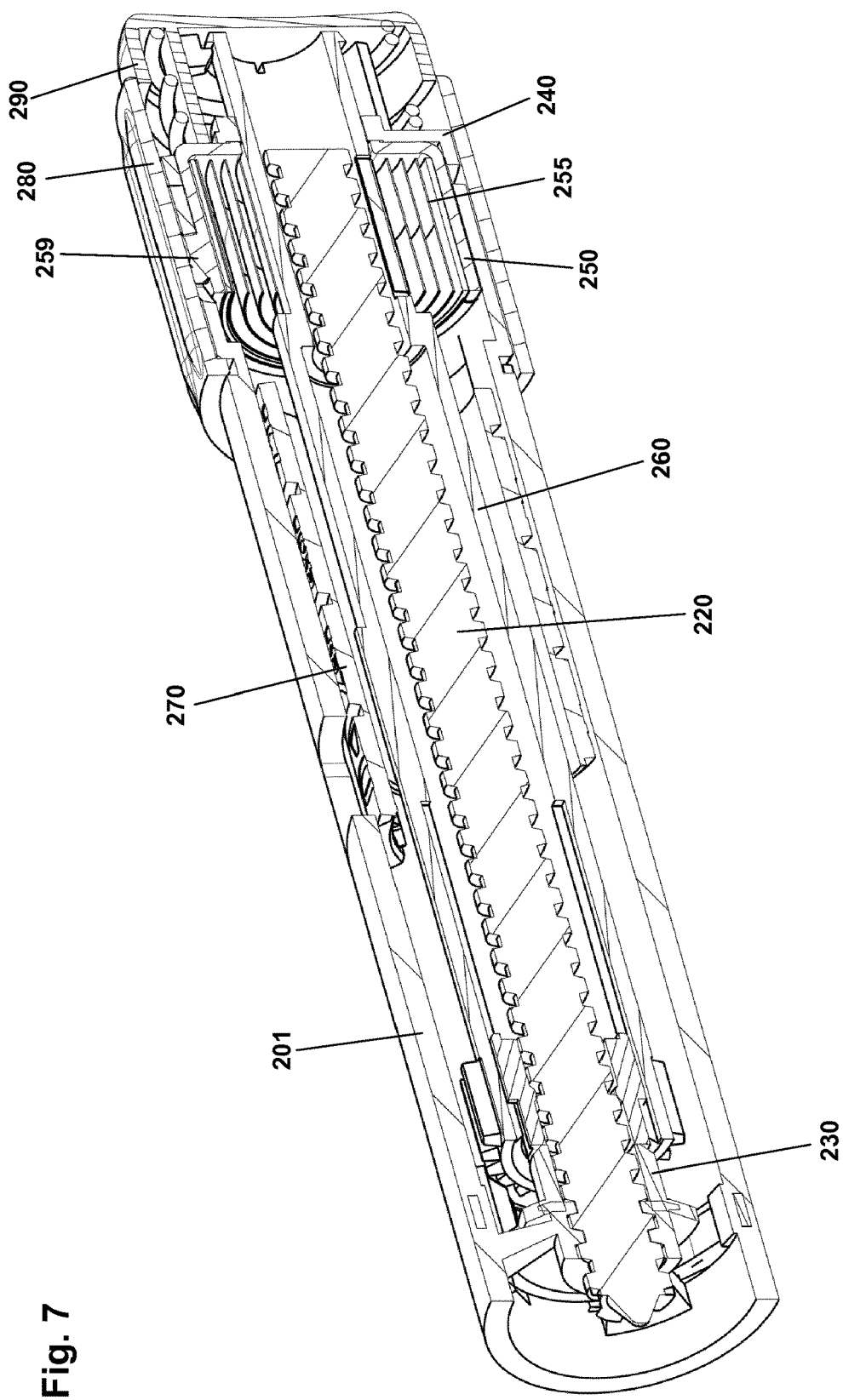
FIG. 7 shows in cross-section the exemplary embodiment in an assembled state.

Turning to FIG. 7 the figure shows the device of FIG. 6 with further components of the dose setting and expelling mechanism arranged inside the housing 201. More specifically, the figure shows a drive tube 260 in splined connection with the scale drum 270, a non-helical clock-type torsion drive spring 255 mounted in a cup-shaped spring housing 250 and connected to the spring housing respectively the drive tube, a threaded piston rod 220 arranged inside the drive tube and being threadedly connected to a stationary housing nut portion 207, a piston driver 230 arranged non-rotatable but axially moveable on the piston rod, as well as a drive coupling 263 allowing the drive tube to be coupled in and out of engagement with the piston driver. The spring housing comprises a number of oblong lateral projections 259 adapted to be slidingly received in the inclined housing slots 209, this allowing the spring housing and spring to be moved axially back and forth as the drive tube is moved back and forth during actuation, the inclined slots together with the spring torque ensuring that the spring housing and associated structures will be moved proximally when the device is not actuated (see below). The device further comprises an end-of-content member 225 coupled to the piston rod and drive tube.

To expel a set dose of drug the actuation button 290 is moved distally against the axial forces of the return spring and the drive spring whereby firstly the distal end of the drive tube 260 engages the piston driver 230 via the drive coupling and secondly the drive tube splines disengages the transmission member splines 242, this allowing the strained spring 255 to rotate the drive tube and thereto coupled piston driver and piston rod 220 counter-clockwise, this resulting in the piston rod being moved distally through the threaded housing nut 207. When the user releases the pressure on the actuation button the return spring and the drive spring serve to return the button and drive tube in the proximal direction and thereby firstly re-engage the splined connection between the drive tube and the transmission member and secondly dis-engage the drive tube from the piston driver, this movement also allowing a partly expelled dose to be paused.

Figure 8:
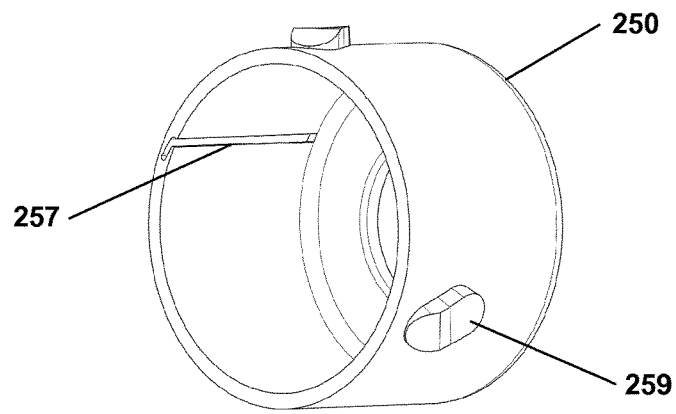
FIG. 8 shows a spring housing of the exemplary embodiment.

FIG. 8 shows in detail the cup-shaped spring housing 250 comprising a number (here: three) of inclined oblong projections 259 on the circumferential outer surface as well as an inner axial slot 257 for attaching the outer end of the drive spring.

Figure 9:
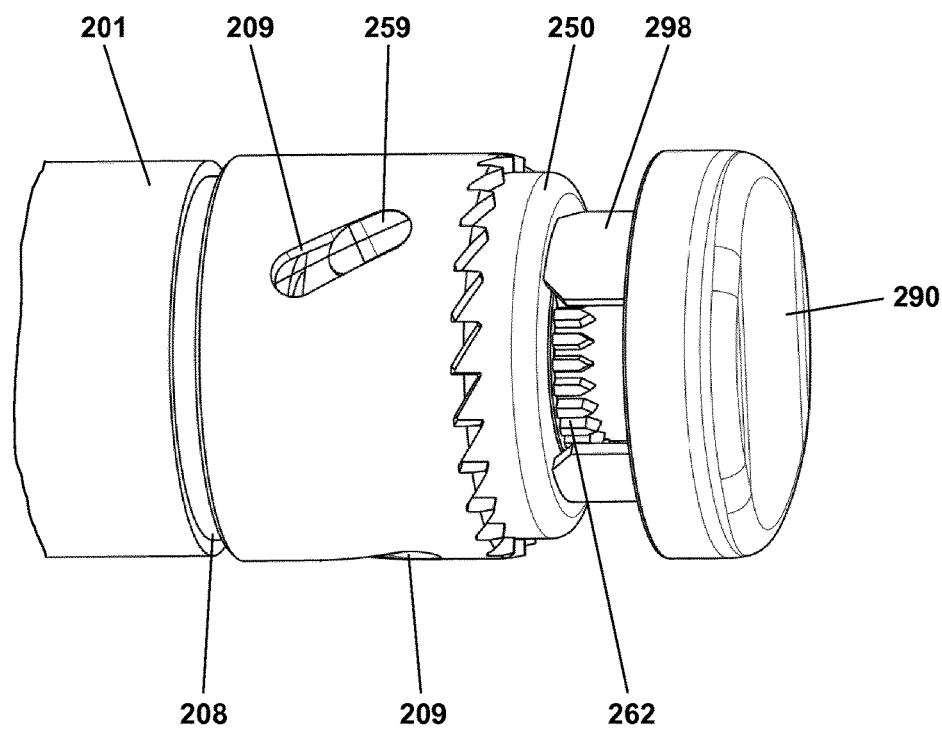
FIG. 9 shows the spring housing mounted in the partially assembled exemplary embodiment.

FIG. 9 shows the proximal part of the assembled device of FIG. 7 with the dose setting member 280 and the transmission member 240 removed, this better showing how the spring housing projections 259 are received in the housing member inclined slots 209 providing a helical guide. The clock-type torsion spring 455 (see FIG. 7) is mounted in the spring housing 450 with the inner end arranged in the drive tube axial slot 267 and the outer end arranged in the spring housing axial slot 257. When the torsion spring during dose setting is winded up and the drive tube is prevented from rotating backwards by the ratchet, the unwinding force of the spring will try rotating the spring housing which due to the helical relationship with the housing will be biased in the proximal direction. When during actuation the actuation button, the drive tube and the spring housing are moved distally the drive spring will be further winded up as the spring housing rotates slightly due to the helical coupling with the housing member. When pressure on the actuation button is released the torque from the drive spring will return the spring housing, the actuation button and the thereto coupled drive tube to their initial proximal-most position.

By this arrangement the return spring 295 can be optimized for the ratchet function as the drive spring provides the additional force to securely and reliably return the drive tube and actuation button after actuation.

Figure 10:
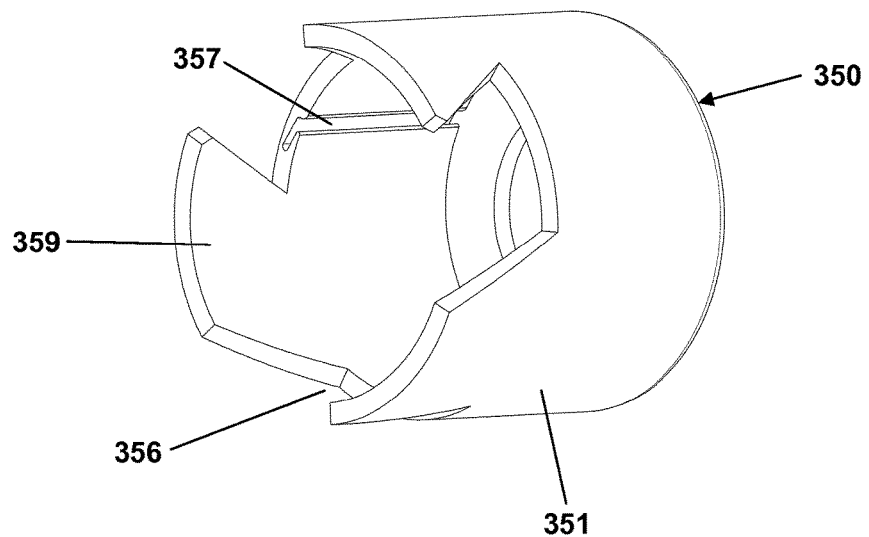
FIG. 10 shows a second embodiment of spring housing for a drug delivery device.

Turning to FIG. 10 a further embodiment of a cup-shaped spring housing 350 is shown. The tubular portion 351 comprises a number (here: three) of distally-facing inclined fingers 359 with corresponding inclined slots 356 formed there between. On the inner surface an axial slot 357 for attaching the outer end of a drive spring is formed. The fingers and slots are adapted to cooperate with corresponding inclined slots 309 and fingers 306 formed in a tubular housing member.

Figure 11:
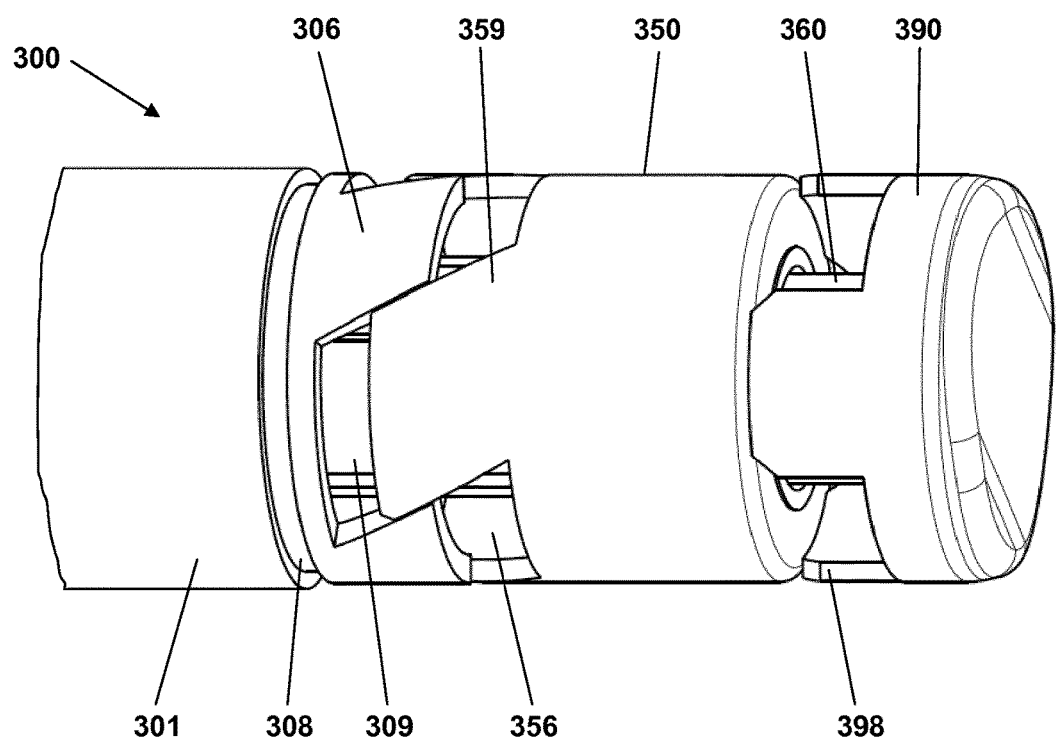
FIG. 11 shows the spring housing of FIG. 10 mounted in a partially assembled second embodiment of a drug delivery device.

FIG. 11 shows the proximal part of a partially assembled drug delivery device 300 comprising a tubular housing member 301, the above-described spring housing 350, a release button 390 and a drive tube 360. In contrast to the above-described embodiment the shown drug delivery device of FIG. 11 may comprise a ratchet mechanism arranged distally in the pen body, e.g. of the type shown in WO 2014/161952 which is hereby incorporated by reference. The drive tube has a proximal-most initial position corresponding to the dose setting state.

The housing member comprises three inclined slots 309 formed between inclined fingers 306, the housing slots being adapted to receive the spring housing fingers and the housing fingers being adapted to be received in the spring housing slots, a helical coupling corresponding to the helical coupling shown in FIG. 9 thereby being formed. In the shown embodiment the fingers and slots have approximately the same width. The housing further comprises a circumferential groove 308 adapted to rotationally engage a dose setting member (not shown).

As in the FIG. 9 embodiment a torque spring is arranged between and connected to the drive tube respectively the spring housing. The release button 390 is connected to the drive tube (e.g. corresponding to FIG. 7) and comprises a number of leg portions 398 providing a proximal support and thereby a stop for the spring housing, this securing the slotted connection between the spring housing and the housing member. A number of openings are formed between the release button leg portions allowing inwardly extending arms from a mounted dose setting member to engage the drive tube and rotate it during dose setting.

By this arrangement the drive spring provides the force necessary to securely and reliably return the drive tube and actuation button after actuation, whereby the traditional actuation button return spring can be dispensed with, e.g. as used in the drug delivery device described in above-referred WO 2014/161952.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification. For example, a traditional helical torsion drive spring may be used.

The invention claimed is:

1. A drug delivery device comprising or adapted to receive a drug-filled cartridge, comprising:
   a housing,
   an expelling assembly comprising:
      a piston rod adapted to engage and axially displace a piston in a received cartridge in a distal direction to thereby expel a dose of drug from the cartridge,
      a drive member defining an axis,
      a spring housing,
      a torsion drive spring coupled to the spring housing and respectively the drive member,
      dose setting means allowing a user to simultaneously set a dose amount to be expelled and strain the drive spring correspondingly by rotation of the drive member, comprising:
         a dose setting member which during dose setting is rotationally coupled to the drive member and adapted to rotate in a first direction to set a dose, and
         a ratchet mechanism allowing the drive member to be held in a set rotational position against the bias of the strained torsion drive spring,
      release means adapted to release the strained torsion drive spring to rotate the drive member to expel the set dose amount, the release means comprising a release member being axially moveable relative to the housing between a proximal initial position and an actuated distal release position,
   wherein:
      the torsion drive spring housing is helically coupled to the housing, the spring exerting a tangential force on the spring housing to thereby bias the spring housing in the proximal direction,
      the spring housing exerts a proximally directed biasing force on the release member when actuated, and
      the spring housing can be moved helically in the distal direction when a distally directed force is exerted on the release member.

2. A drug delivery device as in claim 1, wherein the release member is axially fixed relative to the drive member.

3. A drug delivery device as in claim 1, wherein the dose setting member is adapted to rotate in an opposed second direction to reduce a set dose.

4. A drug delivery device as in claim 3, wherein the ratchet mechanism can be adjusted in both the first and the second direction.

5. A drug delivery device as in claim 4, wherein the ratchet mechanism is in the form of a two-way ratchet mechanism allowing a set dose to be diminished.

6. A drug delivery device as in claim 4, wherein the ratchet mechanism is in the form of a releasable one-way ratchet mechanism allowing a set dose to be diminished.

7. A drug delivery device as in claim 1, wherein the spring housing is helically coupled to the housing by means of protrusions received in corresponding inclined slots.

8. A drug delivery device as in claim 7, wherein the inclined slots are formed in the housing.

9. A drug delivery device as in claim 1, wherein the spring housing is helically coupled to the housing by means of:
   proximally open inclined slots extending from the housing, and
   distally extending inclined fingers extending from the spring housing and adapted to slidingly engage the inclined slots.

10. A drug delivery device as in claim 1, wherein the torsion drive spring is pre-strained.

* * * * *